United States Patent
Morningstar

(10) Patent No.: US 11,607,333 B2
(45) Date of Patent: *Mar. 21, 2023

(54) CORE TRAINING SUIT FOR SCOLIOSIS

(71) Applicant: ScolioSMART, LLC, Lititz, PA (US)

(72) Inventor: Mark William Morningstar, Davison, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 17/556,204

(22) Filed: Dec. 20, 2021

(65) Prior Publication Data

US 2022/0110777 A1 Apr. 14, 2022

Related U.S. Application Data

(62) Division of application No. 16/408,025, filed on May 9, 2019, now Pat. No. 11,246,732.

(60) Provisional application No. 62/669,190, filed on May 9, 2018.

(51) Int. Cl.
*A61F 5/02* (2006.01)

(52) U.S. Cl.
CPC .............. *A61F 5/026* (2013.01); *A61F 5/024* (2013.01); *A61F 5/028* (2013.01)

(58) Field of Classification Search
CPC ...... A61F 5/02–03; A61F 5/37; A61F 5/3715; A61F 5/01–0193; A61F 5/24–34; A61F 13/06–062; A61F 13/14–148; A63B 69/0057–0062
See application file for complete search history.

(56) References Cited

U.S. PATENT DOCUMENTS

| | | | | |
|---|---|---|---|---|
| 1,043,648 A * | 11/1912 | Weaver | ................... | A61F 5/028 602/19 |
| 5,599,286 A * | 2/1997 | Labelle | ................... | A61F 5/024 602/5 |
| 8,795,213 B2 * | 8/2014 | Mills | ....................... | A61F 5/024 128/869 |

* cited by examiner

*Primary Examiner* — Michelle J Lee
(74) *Attorney, Agent, or Firm* — Steve O'Donnell

(57) ABSTRACT

A core muscle strengthening suit for scoliosis is described. The suit uses pieces of material constructed and assembled to transfer force generated by the wearer while walking to rotate the wearer's trunk in the direction of an existing axial twist to exercise and strengthen countervailing muscles in an attempt to maintain a normal gait. The resulting stronger rotational muscles persist in pulling the wearer's spine into alignment when the suit is removed.

2 Claims, 6 Drawing Sheets

CORE TRAINING SUIT FOR SCOLIOSIS

FIELD OF THE INVENTION

Figure 1:
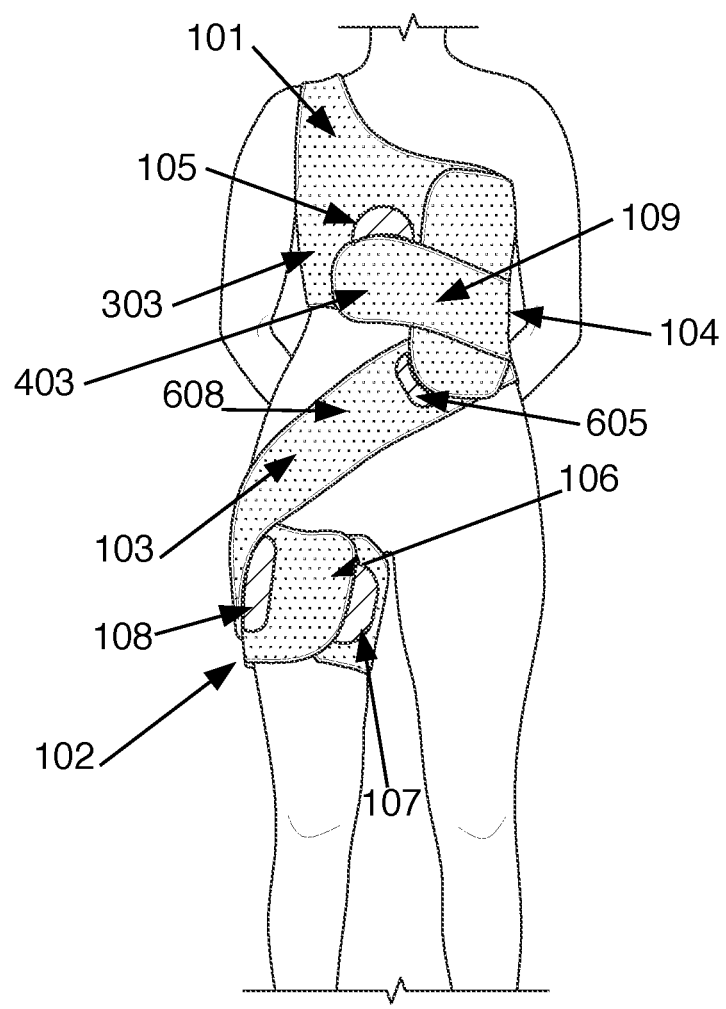

The subject matter of this application concerns methods and devices for correcting spinal curvatures (scoliosis). More particularly, the subject matter of this application pertains to methods and devices for strengthening certain core muscles which are attached to a human spine. Even more particularly, the subject matter of this application pertains to a scoliosis activity suit which strengthens certain core muscles including the transversus abdominis and obliques by using force generated by walking to rotate the torso of the wearer in one direction thereby forcing the core muscles of the wearer to contract in the opposite direction of said force in an attempt to maintain a normal gait; strengthening of these muscles should cause them to continue to contract when the suit is removed, thereby causing the musculature of the patient to pull their spine into proper alignment even when said suit is removed.

BACKGROUND

Ideally, the spine appears straight when viewed from a person's backside, however that is not always the case. In most cases of spinal curvature one or more vertebral sections are axially rotated and such curvatures are commonly called scoliosis. The exact etiology of scoliosis is currently unknown and may be a common symptom to several underlying causes.

A spinal curvature may be so minor that intervention is unnecessary, or it may be so pronounces that the afflicted person is strikingly bent. In addition to physical deformities, a person with scoliosis is at greater risk for back pain and abdominal soreness and often also exhibit mobility problems. Often a mild scoliosis will worsen over time so preventative measures are recommended to prevent or lessen the gradual bend increase.

Most scoliosis correction braces are bulky and challenging to wear during a typical day. Such braces typical apply pressure intended to force the spine into a more ideal shape, however although the application of such forces may straighten a spine, they can also increase the spinal rotation. Stokes, *Mechanical modulation of spinal growth and progression of adolescent scoliosis*, Stud. Healthy Technol Inform. 2008; 135:75-83.

Core muscle strengthening exercises are often recommended for those with scoliosis as stronger core muscles will mitigate back pain, and may pull the spine into alignment.

Other suits which are lower profile and easier to wear such the subject matter of US 2018/0140454, similarly attempt to correct a spinal rotation by applying a force opposite to that of the spinal bend (i.e., a clockwise force applied to correct a counter-clockwise spinal rotation). Although perhaps useful to receive discomfort while it is worn, such devices do little or nothing to strengthen the patient's core muscles so the benefits of such a suit may be short-lived after the suit is removed.

SUMMARY

The subject matter of this application pertains to methods and devices for strengthening core muscles. More particularly, the subject matter of this application pertains to a suit which generates a force which pulls the wearer's trunk to rotate. Even more particularly, the suit captures and redirects force generated by the wearer's locomotion and uses this force to pull the wearer's trunk. A suit as described may either be made to generate a clockwise rotational force or a counter-clockwise rotational force. The forces applied to the wearer cause the wearer's core muscle to engage and pull in the opposite direction to maintain a normal gait. To be maximally useful for scoliosis patients, the direction of the force generated by the suit should be in the same direction as the spinal twist, thereby engaging counter-rotational muscles causing them to strengthen which may help correct the spinal rotation even when the suit is removed.

BRIEF DESCRIPTION OF THE ILLUSTRATIONS

Figure 2:
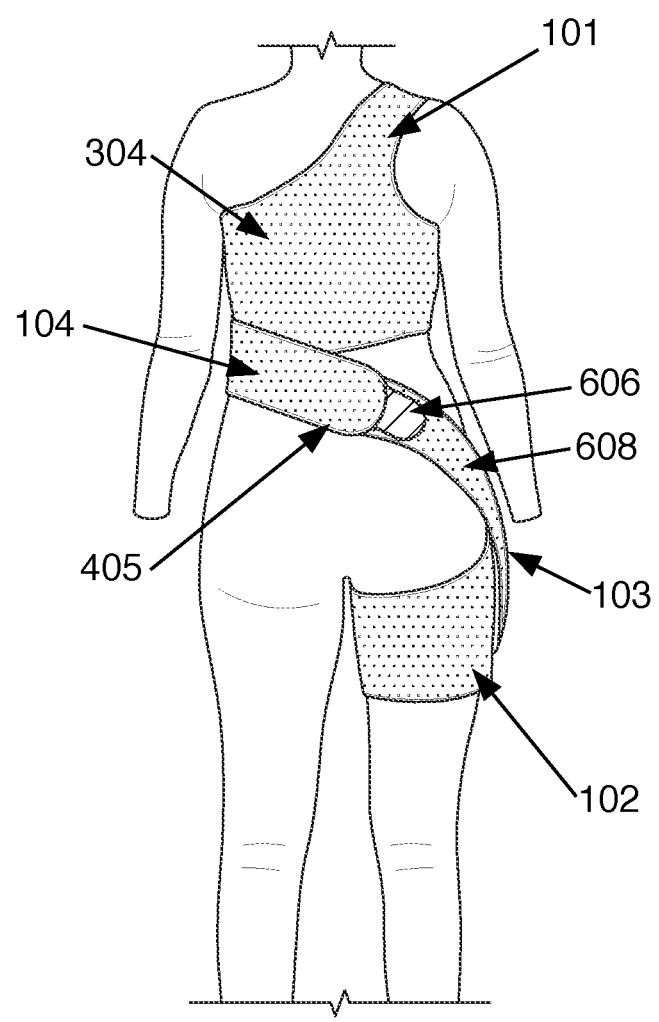
Figure 3:
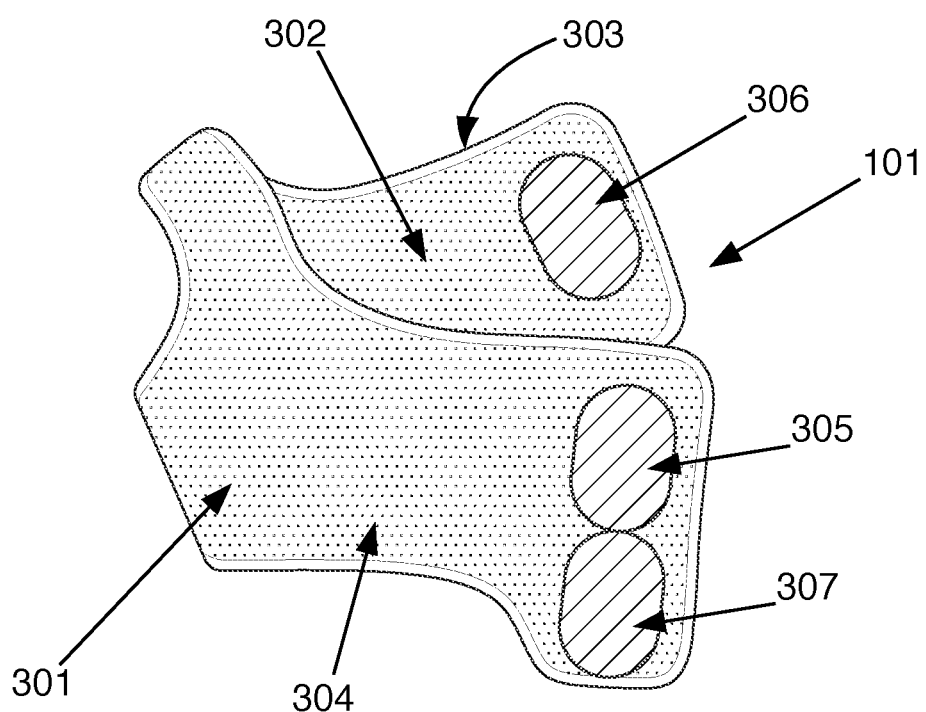
Figure 4:
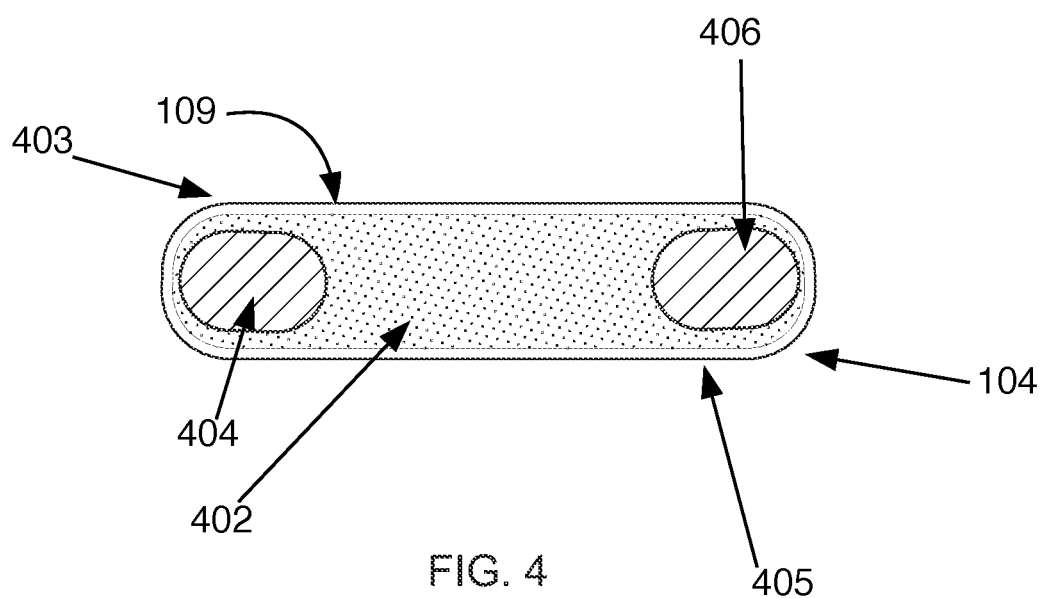
Figure 5:
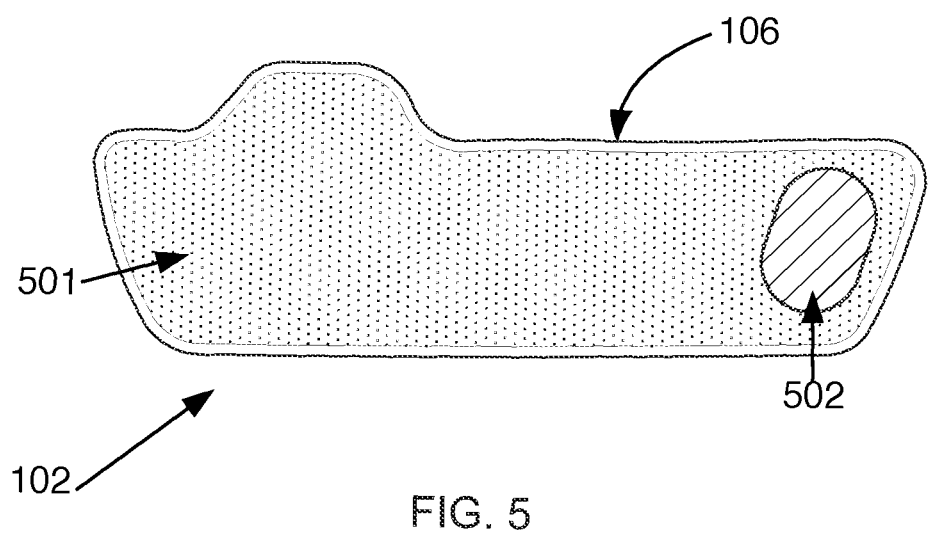
Figure 6:
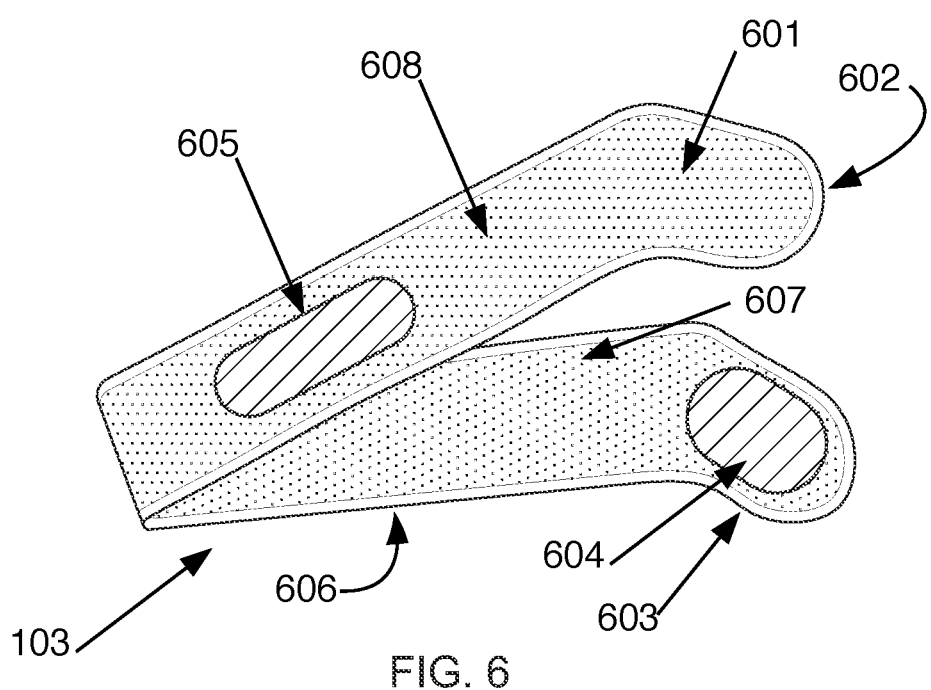

FIG. 1 is a view of the disclosed suit from the front of a patient.
FIG. 2 is a view of the disclosed suit from the back of a patient.
FIG. 3 is a view of a vest portion.
FIG. 4 is a view of a tension strap.
FIG. 5 is a view of a leg portion.
FIG. 6 is a view of a belt portion.

DETAILED DESCRIPTION

The following description and drawings referenced therein illustrate embodiments of the application's subject matter. They are not intended to limit the scope of any claim. Those familiar with the art will recognize that other embodiments of the disclosed method are possible. All such alternative embodiments should be considered within the scope of the application's disclosure.

Accordingly, details on suit assembly or exact components should not be imputed to narrow the scope of any claim.

Each reference number consists of three digits. Reference numbers are not necessarily discussed in the order of their appearance in the figures. Drawings are not to scale.

As used, a right handed scoliosis is a clockwise twist in the patient's spine when viewed form the top of the head. A left-handed scoliosis is the opposite. As used to refer to the disclosed suit, the adjective inelastic is used to describe the quality of something that resists stretching when a linear force is applied.

A core muscle strengthening suit for scoliosis patients is comprised of a vest portion (101), a leg portion (102), a belt portion (103), and a tension strap (104). In most preferable embodiments, at least the belt portion and tension strap are comprised of a flexible, but inelastic material capable of being used as intended without tearing such as, e.g., a fabric covered neoprene.

Said vest portion comprises an outer face (301), an inner face (302), a front (303), a back (304) and a two-component reversible attachment means (305, 306) which allow the vest portion to be secured to itself and worn by a patient. In a most preferred embodiment, said reversible attachment means is comprised of a hook and loop attachment system. Said vest portion further comprises a belt attachment means (307) and a tension strap attachment means (105). In preferred embodiments, the belt attachment means of the vest portion and the tension strap attachment means of the vest portion each comprise one component of a two component hook and loop attachment system.

Said leg portion comprises an outer face (106), an inner face (501) and a reversible attachment means (107, 502) which allow the leg portion to be secured to itself and worn by a patient. In a most preferred embodiment, said reversible attachment means is comprised of a hook and loop attachment system. Said outer surface of the leg portion further comprises a belt attachment means (108). In preferred embodiments, the belt attachment means of the leg portion, and the tension strap attachment means of the vest portion, each comprise one component of a two component hook and loop attachment system.

Said belt portion comprises a first end (601) comprising a first attachment means (602), a second end (603) comprising a second attachment means (604), a vest attachment means (605), a rostral tension strap attachment means (606). an inside face (607), and an outside face (608). Further, when worn, said belt portion comprises a front surface and a back surface such that said front surface comprises the vest attachment means and said back surface comprises the rostral tension strap attachment means. In preferred embodiments, said first and second attachment means of the belt, the rostral tension strap attachment means, and the vest attachment means are each composed of a one component of a two component hook and loop attachment system.

Said tension strap is composed of an outside face (109), an inside face (402), a first end (403) comprising a vest portion attachment means (404), and a second end (405) comprising a belt portion attachment means (406).

In some preferred embodiments, a core muscle strengthening suit for scoliosis patients further comprises a second tension strap. A second tension strap is constructed and is used substantially the same as the previously disclosed tension strap.

In order to describe how one would wear the subject matter of this application and how the subject matter of this application works references are made to the patient's right or left side, the force vector of the tension band, as well as whether the scoliosis of said patent is right-handed or left-handed. It should be evident that such spatial references may be reversed depending on the needs of the patient. Accordingly described is a patient having a left-handed scoliosis in their spine. References to right or left are reversed in those patients with a right-handed scoliosis.

To wear the subject matter of this application, the leg portion is wrapped around the patient's right thigh and secured to itself by said reversible attachment means of the leg portion. The vest portion is worn by the patient and secured to itself by said reversible attachment means of the vest portion such that the front of the vest portion is against the patient' chest. The first end of the belt portion is attached to the belt attachment means of the leg portion and wrapped over the abdomen and the left hip of the patient. The second end of the belt portion extends across the backside of the patient and is also attached to the belt attachment means of the leg portion. The vest attachment mean of the belt portion is reversibly attached to the belt attachment means of the vest located at the left front side of the patient. The said belt portion attachment means of the tension strap is composed of one component of a hook and loop system and is fixed to a corresponding component of the hook and loop system located on the rostral tension strap attachment means of the belt, and finally the vest portion attachment means of the tension strap is composed of one component of a hook and loop system that is wrapped over the front of the patient and fixed to a corresponding component of the hook and loop system of the tension strap attachment means of the vest portion on the right side of the patient. When properly worn, in the front of the patient, the tension strap is largely parallel to the girdle of the patient while at the rear of the patient, the tension straps is parallel the that portion of the belt extending down to the belt attachment means of the leg portion.

In operation, the patient walks as they would normally, however with each right-leg leading step a force is generated which pulls the second end of the belt portion. This force vector is initially parallel the said belt portion, but is changed by the tension strap which redirects the force such that the patient is twisted counter-clockwise. In order to maintain a normal gait, the patient needs to flex certain of their core muscles and an attempt to rotate their core clock-wise with each step to counteract the force generated by the motion of their right leg.

To be maximally effective the rotational force generated by the suit and directed through the tension strap should be in the same direction as the scoliosis. In other words a person having a counter-clockwise or left-handed scoliosis would wear the subject matter of this application as described to force their clock-wise or right-handed rotational core muscles to engage. With continued use such rotational muscles may become so developed that they exert a constant tension in the opposite direction as the scoliosis and at least partially correct such twist without the need for a corrective suit or brace.

I claim:

1. A core muscle training suit which, when worn, transfers force generated by forward movement of a leg of a wearer during walking to cause rotation of the spine, wherein the core muscle training suit comprises:
   a leg portion, a vest portion, a belt portion, and a tension strap; in which
      a. said leg portion is adapted to be reversibly worn by the wearer,
      b. said vest portion is adapted to be reversibly worn by the wearer;
      c. said belt portion comprises a front portion, a first terminal end, a back portion, and a second terminal end,
         i. the first terminal end of said belt portion being directly attached to said leg portion and said front portion adapted to wrap around a hip of the wearer contralateral to said leg portion such that the belt portion extends directly from the thigh of the leg, around the contralateral hip, and returns to the thigh, where the second terminal end is reversibly and directly attached to the leg portion,
      d. said tension strap having a first region and second region,
         i. said first region directly connecting to the back portion of the belt, and
         ii. said second region directly connecting to said vest portion;
      e. said first region of the tension strap configured to be parallel to the pelvic girdle of the wearer and said second region of the tension strap being parallel to said back portion of the belt;
      f. whereby the forward movement of the leg portion of the core muscle training suit during locomotion is configured to pull the tension strap causing a core of the wearer to rotate toward the side contralateral to said leg portion.

2. A method of strengthening core muscles of a wearer having a spinal rotation comprising the steps of the wearer:
   a. wearing the core muscle suit of claim 1 by
      i. securing the leg portion of the core muscle suit around the thigh contralateral to the direction of the spinal rotation, ii. putting on the vest portion of the core muscle training suit,
iii. attaching the first terminal end of the belt portion to the leg portion,
iv. Wrapping the belt portion around the hip, and
v. Attaching the second terminal end of the belt portion to the leg portion,
vi. Attaching the first region of the tension strap to the belt portion, and attaching the second region of the tension strap to the vest portion,
b. whereby the forward movement of the leg portion of the core muscle training suit during locomotion pulls the tension strap causing the core of the wearer to rotate in the direction of the spinal rotation.

* * * * *